United States Patent
Nishijima et al.

(10) Patent No.: US 7,968,607 B2
(45) Date of Patent: Jun. 28, 2011

(54) SKIN PORE MINIMIZERS AND SKIN ELASTICITY IMPROVERS

(75) Inventors: Takafumi Nishijima, Tochigi (JP); Shinya Amano, Tochigi (JP); Tsutomu Fujimura, Tochigi (JP)

(73) Assignee: Koa Corporation, Tokyo (JP)

( * ) Notice: Subject to any disclaimer, the term of this patent is extended or adjusted under 35 U.S.C. 154(b) by 274 days.

(21) Appl. No.: 12/130,160

(22) Filed: May 30, 2008

(65) Prior Publication Data

US 2008/0234390 A1 Sep. 25, 2008

Related U.S. Application Data

(62) Division of application No. 10/398,654, filed as application No. PCT/JP01/05636 on Jun. 29, 2001, now abandoned.

(30) Foreign Application Priority Data

Oct. 12, 2000 (JP) ................................. 2000-311627

(51) Int. Cl.
  A01N 31/14 (2006.01)
  A61K 31/08 (2006.01)
  C07F 9/02 (2006.01)
(52) U.S. Cl. ........................................ 514/723; 558/183
(58) Field of Classification Search .................. 514/723; 558/183
  See application file for complete search history.

(56) References Cited

U.S. PATENT DOCUMENTS

| | | | |
|---|---|---|---|
| 4,269,786 A | 5/1981 | Berkowitz | |
| 4,425,329 A | 1/1984 | Tsutsumi et al. | |
| 4,504,409 A | 3/1985 | Tsutsumi et al. | |
| 4,510,070 A | 4/1985 | Tsutsumi et al. | |
| 5,117,032 A | 5/1992 | Fabry et al. | |
| 5,415,861 A | 5/1995 | Duffy et al. | |
| 5,646,190 A * | 7/1997 | Martin | 514/724 |

FOREIGN PATENT DOCUMENTS

| | | | |
|---|---|---|---|
| EP | 0 245 756 | | 11/1987 |
| JP | 58-104624 | | 6/1983 |
| JP | 60-60195 | | 4/1985 |
| JP | 64-106890 | | 1/1989 |
| JP | 64016890 | * | 1/1989 |
| JP | 04360830 A | * | 12/1992 |
| JP | 8-73312 | | 3/1996 |
| JP | 10-72336 | | 3/1998 |
| JP | 10072336 A | * | 3/1998 |
| JP | 10-279553 | | 10/1998 |
| JP | 11-116604 | | 4/1999 |
| JP | 11-139957 | | 5/1999 |
| JP | 11-263718 | | 9/1999 |
| JP | 2000-169322 | | 6/2000 |
| JP | 2000-302666 | | 10/2000 |
| JP | 2001-192315 | | 7/2001 |
| NL | 9000639 | | 10/1991 |
| WO | 95/35090 | | 12/1995 |

OTHER PUBLICATIONS

Urata et al, JAOCS, 1996, vol. 73(7), pp. 819-830.
Database CA, AN 103: 92649, XP-002330061, JP 60-061030, Apr. 8, 1985.
Arzneim-Forsch, Drug Res. 1985, vol. 35(I), No. 3, pp. 587-592.
"Cosmetic Handbook", Nikko Chemicals, Co., Ltd., pp. 430, 455-456, Nov. 1996 (partial translation).
Cho et al, Photodermatol Photoimmunol Photomed, (2007) vol. 23, pp. 155-162.
Sugiyama-Nakagiri et al, Arch Dermatol Res, Published online: Jun. 22, 2010 7 pgs.
Scheve, Discovery Health, "How Skin Pores Work", http://health.howstuffworks.com/skin-care/information/anatomy/skin-pores.htm accessed Aug. 26, 2010 1 pg.
Pores, Globusz Publishing, http:www.globusz.com/ebooks/Skin/00000056.htm accessed Aug. 20, 2010 2 pgs.
Acne Treatment Info http://www.google.com/imres?imgurl=htp://www.bioacnetreatments.com/images/index-clip-image00 accessed Aug. 26, 2010 1 p.
What are the Functions of the Skin Pore? http://www.ehow.com/about_5127297_functions-skin-pore.html accessed Aug. 26, 2010 2 pgs.
What Causes Wrinkles, http://dermatology.about.com/cs/beauty/a/wrinklecause.htm accessed Aug. 26, 2010 2 pgs.
Wrinkle/-(skin)—Wikipedia, the free encyclopedia http://en.wikipedia.org/wiki/Wrinkle_(skin) accessed Aug. 26, 2010 3 pgs.

* cited by examiner

Primary Examiner — Johann R Richter
Assistant Examiner — Kendra D Carter
(74) Attorney, Agent, or Firm — Oblon, Spivak, McClelland, Maier & Neustadt, L.L.P.

(57) ABSTRACT

This invention relates to skin pore tighteners each of which comprises, as an active ingredient, a compound represented by the following formula:

$$R^1\text{—OG} \quad (1)$$

wherein $R^1$ represents an alkyl or alkenyl group having 8 to 32 carbon atoms, and OG represents a residual group obtained by removing a hydrogen atom from a hydroxyl group of a polyhydric alcohol, monosaccharide or oligosaccharide at least one hydroxyl group of which has been sulfated or phosphatized, or a salt thereof, and also to skin elasticity improvers each of which comprises, as an active ingredient, a glyceryl ether derivative represented by the following formula:

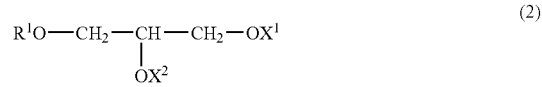

wherein $R^1$ represents the same group as defined above, and $X^1$ and $X^2$ each independently represents a hydrogen atom, —$SO_3OH$ or —$PO(OH)_2$ with the proviso that $X^1$ and $X^2$ are not hydrogen atoms at the same time, or a salt thereof.

5 Claims, No Drawings

SKIN PORE MINIMIZERS AND SKIN ELASTICITY IMPROVERS

TECHNICAL FIELD

This invention relates to skin pore tighteners capable of acting on epidermal cells of the skin and rendering skin pores less conspicuous, and also to skin elasticity improvers capable of preventing and lessening skin wrinkles and sagging.

BACKGROUND ART

Women's skin troubles include wrinkles, sagging, suppleness reductions, pigmentation and conspicuous skin pores, among which wrinkles, sagging and conspicuous skin pores are ranked high. As causes of conspicuous skin pores, there are keratotic plugs formed in skin pores, pigmentation, and the shape of skin pore openings. For keratotic plugs out of these causes, various keratotic plug removers have been developed, and have found wide-spread utility. Use of these keratotic plug removers are, however, accompanied by a drawback in that, even after keratotic plugs have been removed, skin pores are conversely rendered more conspicuous unless they become smaller.

Skin wrinkles and sagging, on the other hand, occur as a result of a loss of skin elasticity upon aging. For their lessening, nothing is practiced except for mere use of collagen-added cosmetic preparations or mere application of astringents or the like, which show temporary serofluid decreasing and vasoconstrictive effects, to local sites. No agent has been found yet to improve skin elasticity.

Therefore, there has been a demand for development of a skin pore tightener capable of tightening skin pores themselves and rendering them less conspicuous and also a skin elasticity improver capable of improving skin elasticity and preventing and lessening skin wrinkles and sagging.

DISCLOSURE OF THE INVENTION

The present inventors have proceeded with an investigation on a possible correlation between the contraction of epidermal cells and the skin. Quite unexpectedly, it has been found that application of an ingredient, which causes strong contraction of keratinocytes, can tighten skin pores and render them less conspicuous. It has also been found that the sulfates or phosphates of alkyl-containing polyhydric alcohols or saccharides induce strong contraction of keratinocytes and are also excellent in skin pore tightening effect and further, that the sulfates or phosphates of alkyl-containing glycerins have superb skin elasticity improving effect and skin tightening effect and are also effective in preventing and lessening skin wrinkles and sagging.

Specifically, the present invention provides a skin pore tightener which comprises a keratinocyte contracting agent as an active ingredient.

The present invention also provides a keratinocyte contracting agent and skin pore tightener, each of which comprises, as an active ingredient, a compound represented by the following formula (1):

$$R^1\text{---}OG \qquad (1)$$

wherein $R^1$ represents an alkyl or alkenyl group having 8 to 32 carbon atoms, and OG represents a residual group obtained by removing a hydrogen atom from a hydroxyl group of a polyhydric alcohol, monosaccharide or oligosaccharide at least one hydroxyl group of which has been sulfated or phosphatized, or a salt thereof.

The present invention also provides a skin elasticity improver and skin tightener, each of which comprises, as an active ingredient, a glyceryl ether derivative represented by the following formula (2):

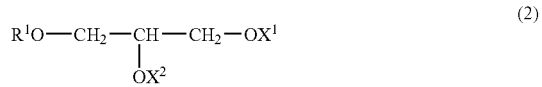

wherein $R^1$ represents the same group as defined above, and $X^1$ and $X^2$ each independently represents a hydrogen atom, $-SO_3OH$ or $-PO(OH)_2$ with the proviso that $X^1$ and $X^2$ are not hydrogen atoms at the same time, or a salt thereof.

The present invention also provides a skin pore tightening method, which comprises applying to the skin a keratinocyte contracting agent or a compound represented by the formula (1) or a salt thereof.

The present invention further provides a method for preventing and/or lessening skin wrinkles and sagging, which comprises applying to the skin a glyceryl ether derivative represented by the formula (2) or a salt thereof.

The present invention still further provides a phosphatized glyceryl ether derivative represented by the following formula (3):

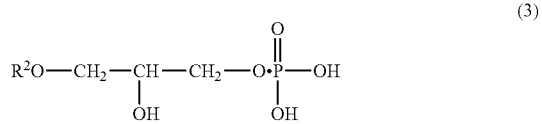

wherein $R^2$ represents isostearyl, 2-hexyldecyl, 2-heptylundecyl, 2-octyldodecyl, 2-decyltetradecyl, 2-dodecylhexadecyl, 2-tetradecyloctadecyl, 2-hexadecyleicosyl or 2-(1,3,3-trimethylbutyl)-5,7,7-trimethyloctyl, or a salt thereof.

BEST MODES FOR CARRYING OUT THE INVENTION

No particular limitation is imposed on the keratinocyte contracting agent for use in the skin pore tightener according to the present invention insofar as it is an ingredient capable of causing contraction of keratinocytes, and examples thereof include, an ingredient which exhibits contracting action on a collagen gel to which human epidermal keratinocytes is attached. Specific examples can include compounds represented by the formula (1) and salts thereof.

In the formula (1), the alkyl group represented by $R^1$ is preferably an alkyl group having 8 to 32 carbon atoms, particularly 10 to 22 carbon atoms, more preferably 16 to 20 carbon atoms. Further, the alkyl group may be either linear or branched although the branched one is preferred from the standpoint of effects. Specific examples can include n-decyl, trimethyldecyl, n-undecyl, 2-heptylundecyl, n-dodecyl, n-tridecyl, n-tetradecyl, n-pentadecyl, n-hexadecyl, n-heptadecyl, n-octadecyl, methylheptadecyl (isostearyl), 2-heptylundecyl, n-nonadecyl, n-icosyl, and n-docosyl. Among these, particularly preferred are branched alkyl groups having 10 to 22 carbon atoms such as isotridecyl, isopalmityl, methylheptadecyl (isostearyl), and 2-heptylundecyl.

Incidentally, an isostearyl group is a mixture of isostearyl groups containing methyl branches at various positions primarily on their respective backbones, because isostearyl alcohol obtained by reducing isostearic acid, which is formed as a byproduct upon production of a dimer acid from beef tallow, soybean oil or the like, is used as a raw material.

The alkenyl group represented by $R^1$ can preferably be a linear or branched alkenyl group having 8 to 32 carbon atoms, with one having 10 to 22 carbon atoms being more preferred. Specific examples can include 10-undecenyl, 9-octadecenyl (oleyl), 9,12-octadienyl, and 13-docosenyl.

In the formula (1), OG represents a residual group obtained by removing a hydrogen atom from a hydroxyl group of a polyhydric alcohol, monosaccharide or oligosaccharide at least one hydroxyl group of which has been sulfated or phosphatized; specifically, residual groups of sulfated or phosphatized polyhydric alcohols, such as sulfated or phosphatized propanediol group, sulfated or phosphatized glyceryl group, and sulfated or phosphatized mannitol group; residual groups of sulfated or phosphatized monosaccharides; and residual groups of sulfated or phosphatized oligosaccharides.

Examples of the polyhydric alcohol can include ethylene glycol, propylene glycol, 1,3-propanediol, glycerin, mannitol, pentaerythritol, and sorbitol, with glycerin being particularly preferred.

Examples of the monosaccharide can include aldopentoses and aldohexoses, such as xylose, arabinose, ribose, glucose, galactose, mannose, talose, idose, altrose, allose and gulose. The oligosaccharide is preferably one having 5 or less constituent monosaccharides from the standpoint of effects, with one having 2 to 3 constituent monosaccharides being particularly preferred. Further, the glycoside bond between each two monosaccharides is preferably (1→2), (1→4) or (1→6), although no limitation is imposed in this respect. In addition, the linkage can be either the α-linkage or the β-linkage.

Examples of the oligosaccharide can include homooligosaccharides such as glucooligosaccharide, galactooligosaccharide, mannooligosaccharide and fructooligosaccharide, oligosaccharides composed of pentoses and hexoses, and oligosaccharides composed of different hexoses. Particularly preferred are oligosaccharides each of which is composed of a repetition of glucose molecules.

There is α/β stereoisomerism in each of the linkages between these monosaccharide or oligosaccharide residual groups and $R^1$. Such stereoisomers are both included in the present invention, but the β-linkage is preferred when the saccharide residual group is galactose residual group.

When OG is a residual group of a sulfated or phosphatized polyhydric alcohol, for example, a sulfated or phosphatized glyceryl group, the compound of the formula (1) is a mono- or disulfate ester or a mono- or diphosphate ester. They can be used either singly or in combination. When OG is a residual group of a sulfated or phosphatized monosaccharide or oligosaccharide, on the other hand, the compound of the formula (1) means such a compound that the hydroxyl groups of the monosaccharide or oligosaccharide moiety except for the 1-hydroxyl group have been sulfated or phosphatized either in part or in whole, to form sulfates or phosphates. From the standpoint of effects, however, one sulfated or phosphatized to an extent of 10 to 30% or so based on the whole hydroxyl groups is preferred.

Examples of the salts of the compounds of the formulas (1), (2) and (3) can include salts with alkali metals such as lithium, sodium and potassium, salts with alkaline earth metals such as beryllium, magnesium and calcium, salts with primary, secondary or tertiary amines, quaternary ammonium salts, and salts with amino acids such as arginine and lysine. Of these, from the standpoint of effects, the sodium salts, potassium salts, quaternary ammonium salts and arginine salts are preferred, with the sodium salts and arginine salts being preferred.

Among such OGs, a sulfated or phosphatized glyceryl group is particularly preferred. In this case, the compound of the formula (1) is a glyceryl ether derivative represented by the following formula (2):

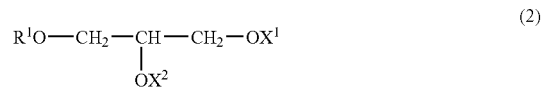

wherein $R^1$ represents the same group as defined above, and $X^1$ and $X^2$ each independently represents a hydrogen atom, —$SO_3OH$ or —$PO(OH)_2$ with the proviso that $X^1$ and $X^2$ are not hydrogen atoms at the same time.

As will be demonstrated in Examples to be described subsequently herein, such glyceryl ether derivatives have skin elasticity improving effect and skin tightening effect in addition to excellent skin pore constricting effect so that they are also usable as skin elasticity improvers and skin tighteners.

Incidentally, phosphatized glyceryl ether derivative have been known to have emulsion stabilizing effect or hypotensive effect (JP-A-58104624, JP-A-60060195, Arzneim.-Forsch./Drug Res., 35(I), Nr. 3, 587-592 (1985)), but are not known at all to have skin pore constricting effect and skin elasticity improving effect.

Among the above-described glyceryl ether derivatives, phosphatized glyceryl ether derivatives in which one of $X^1$ and $X^2$ is —$PO(OH)_2$ and $R^1$ is isostearyl, 2-hexyldecyl, 2-heptylundecyl, 2-octyldodecyl, 2-decyltetradecyl, 2-dodecylhexadecyl, 2-tetradecyloctadecyl, 2-hexadecyleicosyl or 2-(1,3,3-trimethylbutyl)-5,7,7-trimethyloctyl are novel compounds which have not been disclosed yet in any publications.

Among such glyceryl ether derivatives represented by the formula (2), preferred examples can include sulfated glyceryl ether derivatives such as 1-dodecylglycerol-3-sulfate, 1-octadecylglycerol-3-sulfate, 1-isostearylglycerol-3-sulfate and 1-dodecylglycerol-2,3-disulfate, and salts thereof; and phosphatized glyceryl ether derivatives such as 1-decylglycerol-3-phosphate, 1-dodecylglycerol-3-phosphate, 1-tetradecylglycerol-3-phosphate, 1-hexadecylglycerol-3-phosphate, 1-octadecylglycerol-3-phosphate, 1-(2-heptylundecyl)glycerol-3-phosphate, 1-isostearylglycerol-3-phosphate, 1-oleylglycerol-3-phosphate and 1-dodecylglycerol-2,3-diphosphate, and salts thereof. In particular, the arginine salts of 1-(2-heptylundecyl)glycerol-3-phosphate and 1-isostearylglycerol-3-phosphate have high utility because, as will be demonstrated in the Examples to be described subsequently herein, they exhibit outstanding skin pore constricting effect along with excellent skin elasticity improving effect, and are also superb in productivity.

Illustrative, preferred glycoside compounds can include 1-α-O-dodecylglucopyranoside-6-sulfate, 1-β-O-dodecylglucopyranoside-6-sulfate, 1-α-O-(2-heptylundecyl)glucopyranoside-6-sulfate, 1-β-O-(2-heptylundecyl)glucopyranoside-6-sulfate, octadecylglycopyranosidesulfate, 1-α-O-tetradecylgalactopyranoside-6-sulfate, 1-β-O-tetradecylgalactopyranoside-6-sulfate, and the like.

Illustrative, preferred diol compounds can include 1-dodecylpropanediol-3-sulfate, 1-dodecylpropanediol-3-phosphate, and the like.

Further, preferred examples of the polyhydric alcohol can include 1-isostearylmannitol-5-sulfate, 1-isostearylmannitol-5-phosphate, and the like.

The glyceryl compounds in the present invention can each be obtained, for example, by sulfating or phosphatizing a diol ether or glyceryl ether and optionally neutralizing the resultant sulfate or phosphate with an alkali as needed.

For the sulfating reaction, a known sulfating agent, for example, fuming sulfuric acid, concentrated sulfuric acid, sulfamic acid, chlorosulfonic acid, sulfur trioxide, the dioxane or pyridine complex of sulfur trioxide, or the like can be used [Jikken Kagaku Koza (Experimental Chemistry Series) 19, Organic Compound Synthesis I, 201-203]. For the phosphatizing reaction, on the other hand, phosphorus oxychloride, phosphorus trichloride, phosphorus pentachloride, polyphosphoric acid, water-phosphoric acid anhydride, phosphoric acid-phosphoric acid anhydride, or the like can be used [Jikken Kagaku Koza (Experimental Chemistry Series), Organic Compound Synthesis I, 206-210].

The glycoside compounds in the present invention can each be produced based on a known synthesis process [Carbohydro. Res., 230, 245 (1992)]. Among such known synthesis processes, the process in which a sugar peracetate is reacted with an alcohol under acidic condition is preferred for its simplicity. Described specifically, a reducing sugar in which all the hydroxyl groups have been acetylated beforehand, and an alcohol are subjected to glycosidation in the presence of an acid catalyst, and then, hydrolysis is conducted for deacetylation, followed by sulfation or phosphatization.

As will be demonstrated in the Examples to be described subsequently herein, the compounds of the formula (1) thus obtained and their salts have excellent keratinocyte contracting effect, and are useful as keratinocyte contracting agents.

Furthermore, application of the keratinocyte contracting agents to the skin can obtain excellent skin pore tightening effect. Accordingly, the keratinocyte contracting agents are useful as skin pore tighteners.

Among the compounds represented by the formula (1) and their salts, the glyceryl ether derivatives represented by the formula (2) and their salts have excellent skin elasticity improving effect, and are useful as skin elasticity improvers and skin tighteners for the prevention and lessening of skin wrinkles and sagging.

The keratinocyte contracting agents and skin pore tighteners as well as the skin elasticity improvers and skin tighteners is preferably applied to the skin as cosmetic preparations for rendering skin pores, wrinkles and sagging less conspicuous. It is particularly preferred to use them in the form of medicated external skin preparations, such as ointments, or cosmetic external skin preparations, specifically in various forms such as emulsified cosmetic preparations, creams, emulsions, lotions, and gels. Upon formulation of such preparations, it is possible to add, in addition to a compound of the formula (1) or (2) or a salt thereof, those employed commonly in such preparation forms, i.e., oily bases such as vegetable oils and animal oils, antiphlogistics, analgesics, antiseptics, astringents, emollients, hormone preparations, vitamins, humectants, ultraviolet absorbers, alcohols, chelating agents, pH adjusters, preservatives, viscosity increasing agents, colorants, fragrance ingredients, etc. to extents not impairing the advantageous effects of the present invention.

The compound of the formula (1) or (2) or its salt can be added in a proportion of from 0.001 to 20 wt. %, especially from 0.01 to 5 wt. % to the above-described external preparations for the skin.

EXAMPLES

Production Example 1

Production of 1-isostearylglycerol-3-sulfate sodium salt (Compound 3)

Isostearyl glyceryl ether (10 g, 0.029 mol) was dissolved in anhydrous pyridine, and subsequent to cooling with ice, sulfur trioxide-pyridine complex (4.6 g, 0.029 mol) was added. The resulting mixture was stirred for 1 hour under ice cooling, and then stirred at room temperature for 12 hours. After pyridine was distilled off, purified water and sodium hydroxide (1.16 g, 0.029 mol) were added, followed by lyophilization to afford 1-isostearylglycerol-3-sulfate sodium salt (13.8 g).

In a similar manner as in Production Example 1, were obtained 1-dodecylglycerol-3-sulfate sodium salt (Compound 1), 1-octadecylglycerol-3-sulfate sodium salt (Compound 2), 1-α-O-dodecylglucopyranoside-6-sulfate sodium salt (Compound 13), 1-β-O-dodecylglucopyranoside-6-sulfate sodium salt (Compound 14), 1-α-O-(2-heptylundecyl)glucopyranoside-6-sulfate sodium salt (Compound 15), 1-β-O-(2-heptylundecyl)glucopyranoside-6-sulfate sodium salt (Compound 16), dodecylglucopyranosidesulfate sodium salt mixture (Compound 17), octylglucopyranosidesulfate sodium salt mixture (Compound 18), tetradecylglucopyranosidesulfate sodium salt mixture (Compound 19), octadecylglucopyranosidesulfate sodium salt mixture (Compound 20), (2-heptylundecyl)glucopyranosidesulfate sodium salt mixture (Compound 21), methylheptadecylglucopyranosidesulfate sodium salt mixture (Compound 22), 1-α-O-tetradecylgalactopyranoside-6-sulfate sodium salt (Compound 23), 1-β-O-tetradecylgalactopyranoside-6-sulfate sodium salt (Compound 24), and 1-isostearylmannitol-5-sulfate sodium salt (Compound 30).

Production Example 2

Production of 1-isostearylglycerol-3-phosphate disodium salt (Compound 9)

Isostearyl glyceryl ether (5 g, 0.015 mol) was dissolved in hexane, and 105% polyphosphoric acid (6.8 g, 0.075 mol) was added at 50° C., followed by stirring at 70° C. for 12 hours. Subsequently, distilled water (10 g) was added, and the resulting mixture was stirred for 3 hours. After the mixture was allowed to cool down, ethanol was added, and the water layer was separated off. After the organic layer was concentrated, purified water and sodium hydroxide were added, followed by lyophilization to afford 1-isostearylglycerol-3-phosphate disodium salt (7.1 g).

Production Example 3

Production of 1-(2-heptylundecyl)glycerol-3-phosphate disodium salt (Compound 28)

Using 2-heptylundecyl glyceryl ether, production was conducted in a similar manner as in Production Example 2 to afford 1-(2-heptylundecyl)glycerol-3-phosphate disodium salt.

In a similar manner as in Production Examples 2 and 3, were obtained 1-decylglycerol-3-phosphate disodium salt (Compound 4), 1-dodecylglycerol-3-phosphate disodium salt (Compound 5), 1-tetradecylglycerol-3-phosphate disodium salt (Compound 6), 1-hexadecylglycerol-3-phosphate disodium salt (Compound 7), 1-octadecylglycerol-3-phosphate disodium salt (Compound 8), 1-oleylglycerol-3-phosphate disodium salt (Compound 10), and 1-isostearylmannitol-5-phosphate disodium salt (Compound 29).

Production Example 4

Production of 1-dodecylglycerol-2,3-disulfate sodium salt (Compound 11)

Dodecyl glyceryl ether (10 g, 0.039 mol) was dissolved in anhydrous pyridine, and at room temperature, sulfur trioxide-pyridine complex (31 g, 0.195 mol) was added. The resulting mixture was stirred at 70° C. for 1 hour. After pyridine was distilled off, purified water and sodium hydroxide were added, followed by lyophilization to afford 1-dodecylglycerol-2,3-disulfate sodium salt (11.5 g).

Production Example 5

Production of 1-dodecylglycerol-2,3-diphosphate disodium salt (Compound 12)

Dodecyl glyceryl ether (2 g, 7.7 mmol) was dissolved in anhydrous pyridine, and at −20° C., diphenylphosphoric acid chloride (10.4 g, 0.0387 mol) was added dropwise over 1 hour. Subsequent to stirring at the same temperature for 48 hours, deionized water (0.75 g) was added, and pyridine was distilled off under reduced pressure. The residue was extracted with ethyl ether. The extract was washed successively with dilute hydrochloric acid and water, and ethyl ether was distilled off. The residue was then subjected to column chromatography to afford a reaction intermediate (2.63 g).

The reaction intermediate (0.5 g, 0.69 mmol) was then dissolved in acetic acid, and subsequent to addition of platinum oxide (0.2 g), stirring was conducted at room temperature for 3 hours while bubbling hydrogen. Platinum oxide was filtered off, and acetic acid was distilled off. Purified water and sodium hydroxide were then added. Subsequent to lyophilization, the lyophilizate was washed with methanol to afford 1-dodecylglycerol-2,3-diphosphate disodium salt (0.33 g).

Production Example 6

Production of 1-dodecylpropanediol-3-sulfate sodium salt (Compound 25)

1-dodecylpropanediol (0.5 g, 1.8 mmol) was dissolved in anhydrous pyridine, and subsequent to ice cooling, sulfur trioxide-pyridine complex (0.58 g, 3.6 mmol) was added. The resulting mixture was stirred under ice cooling for 1 hour. The mixture was then stirred at room temperature for 12 hours. After pyridine was distilled off, purified water and sodium hydroxide (0.072 g, 1.8 mmol) were added, followed by lyophilization to afford 1-dodecylpropanediol-3-sulfate sodium salt (0.6 g).

Production Example 7

Production of 1-dodecylpropanediol-3-phosphate disodium salt (Compound 26)

1-Dodecylpropanediol (0.5 g, 1.8 mmol) was dissolved in hexane, and 105% polyphosphoric acid (0.85 g, 9 mmol) was added at 50° C., followed by stirring at 70° C. for 12 hours. Subsequently, distilled water (10 g) was added, and the resulting mixture was stirred for 3 hours. After the mixture was allowed to cool down, ethanol was added, and the water layer was separated off. After the organic layer was concentrated, purified water and sodium hydroxide were added, followed by lyophilization to afford 1-dodecylpropanediol-3-phosphate disodium salt (0.66 g).

Production Example 8

Production of dodecylglucopyranosidephosphate disodium salt mixture (Compound 27)

A dodecylglucopyranoside mixture (1.0 g, 2.9 mmol) was dissolved in chloroform, and anhydrous pyridine (0.54 g, 6.8 mmol) was added. After the resulting mixture was cooled to −20° C., phosphorus oxychloride (0.88 g, 5.7 mmol) was added, followed by stirring for 4 hours. Subsequently, the mixture was poured into a great deal of iced water, ethanol was added, and the thus-obtained mixture was then homogenized. The mixture was neutralized to pH 8.5 with sodium hydroxide, and the solvent was distilled off. After the resultant residue was dissolved in ethanol, insoluble matter was removed, and the solvent was distilled off again to afford dodecylglucopyranosidephosphate disodium salt mixture (1.20 g, 2.54 mmol).

Production Example 9

Production of 1-isostearylglycerol-3-phosphate monoarginine salts (Compounds 31-A, 31-B)

95% Phosphoric acid (47.4 g, 0.459 mol) was mixed in toluene (150 mL), and isostearyl glycidyl ether (50 g, 0.153 mol), which had been produced using beef-tallow-derived isostearyl alcohol as a raw material, was added dropwise at room temperature over 30 minutes under nitrogen. The resulting mixture was then stirred further for 2 hours, distilled water (50 g) and isopropyl alcohol (25 g) were added, and the water layer was separated off. The organic layer was washed with a 2.5% aqueous solution of sodium sulfate, and the organic layer was concentrated to obtain crude 1-isostearylglycerol-3-phosphate. The crude 1-isostearylglycerol-3-phosphate so obtained was dissolved in an ethanol-hexane mixed solvent. At 50° C., L-arginine (26.65 g, 0.153 mol) was added gradually, followed by stirring at 70° C. for 2 hours. Insoluble matter was removed by filtration, the filtrate was gradually added into acetone which had been cooled to 10° C. or lower, and precipitated white powder was washed with acetone and then dried to afford 1-isostearylglycerol-3-phosphate monoarginine salt (66.0 g, 72% yield). Using isostearyl glycidyl ether that had been produced using soybean-derived isostearyl alcohol as a raw material, 1-isostearylglycerol-3-phosphate monoarginine salt (Compound 31-B) was obtained likewise.

Production Example 10

Production of 1-(2-heptylundecyl)-glycerol-3-phosphate monoarginine salt (Compound 32)

Using 2-heptylundecyl glycidyl ether, production was conducted in a similar manner as in Production Example 9 to afford 1-(2-heptylundecyl)glycerol-3-phosphate monoarginine salt.

Production Example 11

Production of 1-(2-hexyldecyl)-glycerol-3-phosphate monoarginine salt (Compound 33)

Using 2-hexyldecyl glycidyl ether, production was conducted in a similar manner as in Production Example 9 to afford 1-(2-hexyldecyl)glycerol-3-phosphate monoarginine salt.

Production Example 12

Production of 1-(2-octyldodecyl)-glycerol-3-phosphate monoarginine salt (Compound 34)

Using 2-octyldodecyl glycidyl ether, production was conducted in a similar manner as in Production Example 9 to afford 1-(2-octyldodecyl)glycerol-3-phosphate monoarginine salt.

Production Example 13

Production of 1-[2-(1,3,3-trimethylbutyl)-5,7,7-trimethyloctyl]-glycerol-3-phosphate monoarginine salt (Compound 35)

Using 2-(1,3,3-trimethylbutyl)-5,7,7-trimethyloctyl glycidyl ether, production was conducted in a similar manner as in Production Example 9 to afford 1-[2-(1,3,3-trimethylbutyl)-5,5,7-trimethyloctyl]-glycerol-3-phosphate monoarginine salt.

Production Example 14

Production of 1-dodecylglycerol-3-phosphate monoarginine salt (Compound 36)

Using dodecyl glycidyl ether, production was conducted in a similar manner as in Production Example 9 to afford 1-dodecylglycerol-3-phosphate monoarginine salt.

Production Example 15

Production of 1-tetradecylglycerol-3-phosphate monoarginine salt (Compound 37)

Using tetradecyl glycidyl ether, production was conducted in a similar manner as in Production Example 9 to afford 1-tetradecylglycerol-3-phosphate monoarginine salt.

Production Example 16

Production of 1-hexadecylglycerol-3-phosphate monoarginine salt (Compound 38)

Using hexadecyl glycidyl ether, production was conducted in a similar manner as in Production Example 9 to afford 1-hexadecylglycerol-3-phosphate monoarginine salt.

Production Example 17

Production of 1-octadecylglycerol-3-phosphate monoarginine salt (Compound 39)

Using octadecyl glycidyl ether, production was conducted in a similar manner as in Production Example 9 to afford 1-octadecylglycerol-3-phosphate monoarginine salt.

Production Example 18

Production of 1-oleylglycerol-3-phosphate monoarginine salt (Compound 40)

Using oleyl glycidyl ether, production was conducted in a similar manner as in Production Example 9 to afford 1-oleylglycerol-3-phosphate monoarginine salt.

Production Example 19

Production of 1-(2-decyltetradecyl)-3-phosphate monoarginine salt (Compound 41)

Using 2-decyltetradecyl glycidyl ether, production was conducted in a similar manner as in Production Example 9 to afford 1-(2-decyltetradecyl)glycerol-3-phosphate monoarginine salt.

Production Example 20

Production of 1-(2-dodecylhexadecyl)-glycerol-3-phosphate monoarginine salt (Compound 42)

Using 2-dodecylhexadecyl glycidyl ether, production was conducted in a similar manner as in Production Example 9 to afford 1-(2-dodecylhexadecyl)glycerol-3-phosphate monoarginine salt.

Spectral data on novel compounds out of Compounds 1 to 42 are presented in Table 1.

TABLE 1

| Compound | IR spectrum ($cm^{-1}$, KBr tablet method) | $^1$H-NMR spectrum δ, ppm | Solvent for sample preparation |
|---|---|---|---|
| Compound 3 | 3376, 2932, 2860, 1470, 1270, 1230, 1124 | 4.12-4.01, 3.60-3.40, 1.60, 1.30, 0.89 | $D_2O$-$CD_3OD$ |
| Compound 9 | 3440, 2932, 2860, 1468, 1120, 982 | 4.24, 4.01-3.43, 1.62, 1.31, 0.89 | $D_2O$-$CD_3OD$ |
| Compound 11 | 2932, 2860, 1472, 1270, 1240, 1118 | 4.64, 4.23, 3.74, 3.56, 1.58, 1.28, 0.87 | $D_2O$-$CD_3OD$ |
| Compound 12 | 2932, 2860, 1470, 1106, 982 | 4.23, 3.83, 3.69, 3.57, 1.57, 1.26, 0.85 | $D_2O$-$CD_3OD$ |
| Compound 23 (mixture) | 2924, 2856, 1470, 1252, 1208, 1130 | 3.93, 3.57-3.28, 1.82, 1.65, 1.14, 0.72 | $D_2O$-$CD_3OD$ |
| Compound 24 (mixture) | 2856, 1472, 1254, 1116 | 3.60-3.30, 1.89, 1.58, 1.28, 0.87 | $D_2O$-$CD_3OD$ |

TABLE 1-continued

| Compound | IR spectrum (cm$^{-1}$, KBr tablet method) | $^1$H-NMR spectrum δ, ppm | Solvent for sample preparation |
|---|---|---|---|
| Compound 27 | 3440, 2932, 2860, 1470, 1242, 1096 | 4.44, 4.09, 3.95-3.54, 1.60, 1.24, 0.87 | D$_2$O-CD$_3$OD |
| Compound 28 | 3432, 2932, 2860, 1466, 1090, 978 | 4.10, 3.80-3.22, 1.48, 1.14, 0.75 | D$_2$O-CD$_3$OD |
| Compounds 31-A & 31-B | 3380, 2928, 2860, 1676, 1642, 1470, 1082, 936 | 3.96-3.49, 3.23, 1.90, 1.74-1.14, 0.88 | D$_2$O-CD$_3$OD |
| Compound 32 | 3368, 2932, 2860, 1682, 1646, 1470, 1082, 974 | 3.96-3.22, 1.93, 1.72, 1.31, 0.92 | D$_2$O-CD$_3$OD |
| Compound 33 | 3372, 2932, 2860, 1682, 1644, 1470, 1058, 924 | 3.91-3.24, 1.92, 1.65, 1.29, 0.91 | D$_2$O-CD$_3$OD |
| Compound 34 | 3372, 2932, 2860, 1682, 1638, 1472, 1054, 926 | 3.91-3.24, 1.92, 1.67, 1.30, 0.92 | D$_2$O-CD$_3$OD |
| Compound 35 | 3416, 2932, 2860, 1682, 1648, 1470, 1078, 930 | 3.97-3.28, 1.58, 1.28, 0.87 | D$_2$O-CD$_3$OD |
| Compound 36 | 3396, 2932, 2860, 1684, 1634, 1470, 1062, 972 | 3.71-2.96, 1.67, 1.44, 1.06, 0.65 | D$_2$O |
| Compound 37 | 3376, 2924, 2856, 1678, 1636, 1472, 1054, 928 | 3.67-2.90, 1.67, 1.44-1.33, 1.02, 0.61 | D$_2$O |
| Compound 38 | 3372, 2924, 2856, 1682, 1636, 1472, 1054, 928 | 3.73-3.00, 1.67, 1.48-1.40, 1.07, 0.66 | D$_2$O |
| Compound 39 | 3368, 2924, 2856, 1680, 1636, 1472, 1058, 920 | 3.77-3.01, 1.70, 1.43, 1.10, 0.66 | D$_2$O |
| Compound 40 | 3400, 2932, 2860, 1678, 1636, 1470, 1054, 974 | 5.11, 3.74-3.02, 1.68, 1.37, 1.07, 0.67 | D$_2$O |
| Compound 41 | 3368, 2932, 2860, 1678, 1642, 1470, 1089, 974 | 3.96-3.27, 1.55, 1.26, 0.88 | CDCl$_3$ |
| Compound 41 | 3384, 2928, 2860, 1682, 1646, 1470, 1070, 974 | 3.96-3.28, 1.55, 1.26, 0.88 | CDCl$_3$ |

Example 1

1) After type I collagen ("Cellmatrix Type I-A", Nitta Gelatin), "MCDB 153 medium" (Sigma Chemical Co.), 20 mM HEPES (Wako Pure Chemical Industries) and purified water were thoroughly mixed under ice cooling, 500 μL per well were added to a 24-well plate (Falcon), followed by warming at 37° C. in an incubator to effect gelation. Using MCDB 153 medium, 1 mL aliquots of keratinocytes ("NHEK 6306", Clonetics) were seeded at 2×10$^4$ cells/cm$^2$ onto the collagen gels, respectively. Subsequent to incubation for 24 hours, the collagen gels were peeled off with a pipette tip from the culture dishes. Shortly after that, test substances prepared to a concentration as high as 100 times the final concentration were added 10 μL by 10 μL. Upon elapsed time of 1 hour after the addition, the gels were photographed using a "Minolta α707-si Camera" with "50 Macrolens". Subsequent to development of the pictures, contracted rings were copied onto OHP sheets, the areas inside the contracted rings were determined by image analysis software, "Image-Pro PLUS" (Media Cybanetics, Inc.), and contraction ratios (%) were calculated supposing that the contraction ratio (%) of a control (gel peeling alone) was 100. The results are presented in Table 2.

TABLE 2

| Test substance | Concentration (μM) | Contraction ratio (%) |
|---|---|---|
| Compound 8 | 50 | 77.0 |
| Compound 9 | 50 | 62.3 |
| Compound 14 | 50 | 90.0 |
| Compound 18 | 50 | 90.1 |
| Compound 23 | 10 | 60.7 |
| Compound 24 | 10 | 84.9 |
| Compound 25 | 10 | 88.0 |
| Compound 26 | 1 | 73.5 |
| Compound 27 | 10 | 67.0 |
| Compound 28 | 10 | 48.3 |
| Compound 29 | 10 | 53.3 |
| Compound 30 | 10 | 56.8 |
| Compound 31-A | 10 | 56.6 |
| Compound 31-B | 10 | 56.7 |
| Compound 32 | 10 | 52.2 |
| Compound 33 | 10 | 63.4 |
| Compound 34 | 10 | 67.3 |
| Compound 35 | 10 | 66.9 |
| Compound 36 | 10 | 71.3 |
| Compound 37 | 10 | 63.3 |
| Compound 38 | 10 | 81.4 |
| Compound 39 | 10 | 70.2 |
| Compound 40 | 10 | 63.0 |
| Compound 41 | 10 | 87.3 |
| Compound 42 | 10 | 87.7 |

As evident from Table 2, the compounds of the formula (1) have excellent keratinocyte contracting effect.

Example 2

Three of New Zealand white rabbits (male, about 2.5 kg) which ear skin pores were conspicuous were used. A 2% solution of Compound 9 (solvent: ethanol) was applied onto the left ear of each rabbit, and the solvent was applied onto the right ear of the rabbit as a control site, each on the inner side of the ala, twice a day, 150 μL each time.

Upon elapsed time of 8 weeks after the initiation of the application, the skin was collected, and the size of skin pores was measured by image analysis. Described specifically, each rabbit was sacrificed and then, his ears were collected. A scalpel was inserted into each ear sample around the applied site, and the skin was peeled off above the cartilage. At that time, care was exercised to avoid stretching of the skin. The skin was spread over a cork board and then, subjected to biopsy with a punch of 6 mm in diameter to collect the skin from six (6) locations on each ear. The collection was conducted such that skin samples were obtained from the same locations on both the left and right ears. The skin samples collected by punch biopsy were magnified 40-fold by a videomicroscope (manufactured by HIROX CO., LTD.) while exercising care to avoid drying, and their images were captured. Measurement of skin pores from the captured images was conducted using the image analysis software, "Image-Pro PLUS" (Media Cybanetics, Inc.). Namely, each captured image was converted into an 8-bit gray scale image, which was then binarized using 100 as a threshold. From image elements still remaining after the processing, image elements other than skin pores were eliminated. On the image, the areas of the individual skin pores were measured, so that the skin pore area on each punched skin sample was calculated. An average of the skin pore areas on the six punched skin samples was recorded as the size of skin pores on the corresponding ear sample of the corresponding rabbit.

As a result of calculation of the areas of skin pores on the applied sites of the individual ear samples, the sites applied with Compound 9 had a skin pore area of 0.015 mm$^2$ as opposed to 0.022 mm$^2$, the skin pore area of the control sites, so that the sites applied with Compound 9 were found to be about 30% smaller in skin pore area than the control sites. Based on a significance test conducted by the paired comparison testing method, the test result was determined to be significant with a risk factor of not greater than 5%. In addition, the remaining compounds obtained in the above-described Production Examples also exhibited skin pore contracting effect like Compound 9.

Example 3

Measurement of Collagen Gel Tightening Promoting Ability

Measurement was conducted on the ability to promote the tightening of a fibroblast-embedded collagen gel as a dermis model. The collagen gel was prepared following the procedure reported in a publication [J. Cell Science, 102, 315 (1992) or J. Invest. Dermatol., 93, 792 (1989)]. Described specifically, a solution of HEPES (250 mM) in a 0.05 N sodium hydroxide solution, a 5-fold concentrate of DMEM ("GIBCO DMEM", low glucose), FCS (2%, Fetal Calf Serum) and purified water were added under ice cooling to a collagen gel solution (product of Nitta Gelatin Inc., "type 1-A" (3.0 mg/mL, pH=3)), and finally, a suspension of human skin fibroblasts (derived from a human fore skin) was added. After the resulting mixture was thoroughly stirred to eliminate bubbles, 600 μL per well was added to 24-well dishes, followed by immediate warming at 37° C. in an incubator to effect gelation. Three to four hours later, 1 mL of serum-free DMEM medium was added to each of the wells, and the gels were separated at peripheries thereof from the corresponding dishes and were brought into a floating state. Eighteen hours after that, the medium was replaced with serum-free DMEM media which contained 100 to 10 μM of test substances, respectively, and incubation was conducted further for 48 hours.

Volume measurement of the gels was conducted by a weight measuring method similar to that reported in the publication [J. Cell Science, 102, 315 (1992)]. Described specifically, subsequent to immobilization with 10% formalin (4° C., 24 hours), the surface tension of water was reduced by the addition of Triton X100 (product of Wako Pure Chemical Industries) (1%), and the weights were measured.

Measurement results of relative volumes for the respective compounds as calculated supposing that the volume of the control was 100% are presented in Table 3.

TABLE 3

| Compound | Concentration (μM) | Average gel volume |
|---|---|---|
| Control | | 100 |
| Compound 1 | 10 | 93 |
| | 30 | 85 |
| Compound 2 | 10 | 97 |
| | 30 | 92 |
| Compound 3 | 3 | 86 |
| | 10 | 74 |
| | 30 | 95 |
| Compound 4 | 15 | 96 |
| | 50 | 88 |
| Compound 5 | 15 | 94 |
| | 50 | 83 |
| Compound 6 | 15 | 91 |
| | 50 | 88 |
| Compound 7 | 15 | 94 |
| | 50 | 79 |
| Compound 8 | 15 | 93 |
| | 50 | 77 |
| Compound 31-A | 15 | 94 |
| | 50 | 79 |
| Compound 32 | 15 | 92 |
| | 50 | 75 |

As evident from Table 3, it is understood that under the action of the compounds according to the present invention, the collagen gels were reduced in volume and the tightening of the collagen gels was promoted.

Example 4

Evaluation of Rat Skin Elasticity Improving (Tightening) Effect

Onto the entire dorsal skins of HR rats (WBN/ILA-HT, 7 weeks old), 2% solutions of Compounds 1 and 4 (solvent: 10% ethanol) were applied in the form of spray, respectively, once or twice a day, 7 to 8 times a week in total, in an amount of 0.7 mL each time. As a control, 10% ethanol solution was used. Two weeks later, the skin elasticity of the skin at a central dorsal part at a site slightly rightward of the median line of each HR rat was measured under Nembutal anesthesia by using a cutometer ("CUTOMETER SEM474", Courage+ Khazaka Electronic GmbH). The measurement was conducted by setting the suction pressure, suction time and release time at 100 hpa, 5 seconds and 2 seconds, and an instantaneous elastic displacement Ue, an instantaneous recovery displacement Ur and a final displacement Uf were recorded. Based on changes in the skin elasticity, skin tightening effect was determined. Ue is an index of elasticity, while Uf is an index of softness and malleability. Both of these values decrease on the face or the like upon aging, and also decrease when the skin is in a swollen state. Increases in these values, therefore, can be taken as an indication of a state that the skin is in a tightened state with its softness, melleability and elasticity having been increased further. Ur is also an index of elasticity, and decreases when the skin is in a saggy state or a swollen state. Similarly, an increase in this value serves as an indication of a state that the skin is in a tightened state with its elasticity and tightness having been increased further. Further, Ur/Uf is also an index of the elasticity of the skin, and like Ur, decreases when the skin becomes saggy or is swollen. Moreover, Ur/Uf is known to decrease upon aging irrespective of the face or body site, and is an important index of sagginess. The results are presented in Table 4 and Table 5.

TABLE 4

| Compound | Skin thickness (mm) | Ue | Uf | Ur | Ur/Uf |
|---|---|---|---|---|---|
| Control | 0.835 | 0.100 | 0.154 | 0.698 | 0.457 |
| Compound 1 | 0.820 | 0.113 | 0.159 | 0.834 | 0.540 |

TABLE 5

| Compound | Skin thickness (mm) | Ue | Uf | Ur | Ur/Uf |
|---|---|---|---|---|---|
| Control | 0.753 | 0.200 | 0.248 | 0.088 | 0.371 |
| Compound 4 | 0.725 | 0.225 | 0.275 | 0.109 | 0.401 |

From Table 4 and Table 5, it has been confirmed that Compounds 1 and 4, when applied, increased the skin elasticity and exhibited skin tightening effect.

Formulation Example 1

Toilet Water

A toilet water of the below-described formulation was prepared by a method known per se in the art.

| (Ingredients) | (wt. %) |
|---|---|
| Compound 1 | 2.0 |
| Compound 6 | 0.5 |
| Glycerin | 5.0 |
| Dipropylene glycol | 4.0 |
| Polyoxyethylene (20) isocetyl ether | 1.0 |
| Clove extract | 1.0 |
| Orange peel extract | 1.0 |
| Hiba arborvitae (*Thujopsis dolabrata* var. *Dorabrata*) extract | 0.5 |
| Ethanol | 8.0 |
| Preservative | q.s. |
| Fragrance | q.s. |
| Buffer | q.s. |
| Purified water | Balance |

Formulation Example 2

Cream (W/O)

A cream of the below-described formulation was prepared by a method known per se in the art.

| (Ingredients) | (wt. %) |
|---|---|
| Compound 9 | 2.0 |
| Compound 7 | 1.0 |
| Microcrystalline wax | 3.0 |
| Lanolin | 3.0 |
| Vaseline | 5.0 |
| Squalane | 9.0 |
| Olive oil | 12.0 |
| Sorbitan sesquioleate | 3.0 |
| Polyoxyethylene (20) sorbitan trioleate | 3.0 |
| Barley extract | 2.0 |
| Placenta extract | 1.0 |
| Albutin | 1.0 |
| Kojic acid | 1.0 |
| Phosphatidylcholine | 1.0 |
| Fragrance | q.s. |
| Buffer | q.s. |
| Purified water | Balance |

Formulation Example 3

Cream (O/W)

A cream of the below-described formulation was prepared by a method known per se in the art.

| (Ingredients) | (wt. %) |
|---|---|
| Compound 5 | 2.5 |
| Compound 1 | 0.3 |
| Hardened coconut oil | 6.0 |
| Stearic acid | 3.0 |
| Cetanol | 4.0 |
| Vaseline | 2.0 |
| Squalane | 8.0 |
| Neopentyl glycol dicaprinate | 4.0 |
| Polyoxyethylene (20) sorbitan monostearate | 2.3 |
| Glycerin stearate | 1.7 |
| Glycerin | 3.0 |
| 1,3-Butylene glycol | 7.0 |
| Glycyrrhizic acid | 1.0 |
| Tocopherol | 2.0 |
| Hyaluronic acid | 1.0 |
| Dutch mustard extract | 3.0 |
| *Aloe* extract | 1.0 |
| Carrot extract | 1.0 |
| Preservative | q.s. |
| Fragrance | q.s. |
| Purified water | Balance |

Formulation Example 4

Emulsion

An emulsion of the below-described formulation was prepared by a method known per se in the art.

| (Ingredients) | (wt. %) |
|---|---|
| Compound 1 | 1.5 |
| Compound 7 | 0.3 |
| Palmitic acid | 0.5 |
| Olive oil | 2.0 |
| Cetanol | 1.0 |
| Jojoba oil | 5.0 |
| Sodium monohexadecylphosphate | 2.0 |
| Sorbitan monostearate | 0.5 |
| Glycerin | 15.0 |
| Ethanol | 5.0 |
| Ascorbic acid | 0.5 |
| Tocopherol nicotinate | 1.0 |
| *Zingiber officinale* (ginger) root extract | 2.0 |
| *Ginkgo biloba* extract | 2.0 |

Formulation Example 5

Emulsion

An emulsion of the below-described formulation was prepared by a method known per se in the art.

| (Ingredients) | (wt. %) |
|---|---|
| Compound 9 | 2.0 |
| Compound 3 | 0.8 |
| Compound 1 | 1.2 |
| Stearic acid | 1.0 |
| Cholesteryl isostearate | 2.0 |
| Jojoba oil | 4.0 |
| Squalane | 8.0 |
| Sorbitan sesquioleate | 0.8 |
| Polyoxyethylene (20) sorbitan monostearate | 0.5 |
| 1,3-Butylene glycol | 5.0 |
| L-Arginine | 0.4 |
| Carboxyvinyl polymer | 0.2 |
| Carrot extract | 1.5 |
| *Uncaria Gambir* extract | 0.5 |
| *Corthellus shiitake* (mushroom) extract | 0.5 |
| *Laminaria japonica* extract | 0.5 |
| Ceramide | 1.0 |
| Preservative | q.s. |
| Fragrance | q.s. |
| Purified water | Balance |

Formulation Example 6

Pack

A pack of the below-described formulation was prepared by a method known per se in the art.

| (Ingredients) | (wt. %) |
|---|---|
| Compound 5 | 3.0 |
| Compound 8 | 2.0 |
| Polyvinyl alcohol | 14.0 |
| Carboxymethylcellulose sodium | 3.0 |
| Xanthan gum | 1.0 |
| Glycerin | 3.0 |
| 1,3-Butylene glycol | 2.0 |
| Polyoxyethylene (50) hydrogenated castor oil | 0.5 |
| Japanese angelica root extract | 0.5 |
| Whey extract | 2.0 |
| *Astragalus sinicus* extract | 0.5 |
| Sphingosine | 0.2 |
| Preservative | q.s. |
| Fragrance | q.s. |
| Purified water | Balance |

Formulation Example 7

Toilet Water

A toilet water of the below-described formulation was prepared by a method known per se in the art.

| (Ingredients) | (wt. %) |
|---|---|
| Compound 31-A | 1.0 |
| Glycerin | 5.0 |
| Polyoxyethylene (20) isocetyl ether | 0.1 |
| L-Arginine | 0.6 |
| Tuberose polysaccharide solution | 10.0 |
| Ethanol | 10.0 |
| Preservative | q.s. |
| Fragrance | q.s. |
| Buffer | q.s. |
| Purified water | Balance |

Formulation Example 8

Toilet Water

A toilet water of the below-described formulation was prepared by a method known per se in the art.

| (Ingredients) | (wt. %) |
|---|---|
| Compound 32 | 1.0 |
| Glycerin | 5.0 |
| Polyoxyethylene (20) isocetyl ether | 0.1 |
| L-Arginine | 0.6 |
| Tuberose polysaccharide solution | 10.0 |
| Ethanol | 10.0 |
| Preservative | q.s. |
| Fragrance | q.s. |
| Buffer | q.s. |
| Purified water | Balance |

INDUSTRIAL APPLICABILITY

The skin pore tighteners according to the present invention have excellent effect in tightening skin pores and rendering them less conspicuous, while the skin elasticity improvers and skin tighteners according to the present invention have superb effect in preventing and lessening skin wrinkles and sagging. Accordingly, they are useful as ordinary cosmetic preparations, as cosmetic preparations after depilating treatment, and also as cosmetic preparations after removal of keratotic plugs.

The invention claimed is:

1. A skin pore tightening method, comprising applying, to the skin of a human having conspicuous skin pores in need thereof, a compound represented by the following formula (1), which is a keratinocyte contracting agent:

$$R^1\text{—OG} \quad (1)$$

wherein $R^1$ is an alkyl or alkenyl group having 8 to 32 carbon atoms, and OG is a residual group obtained by removing a hydrogen atom from a hydroxyl group of a polyhydric alcohol or monosaccharide at least one hydroxyl group of which has been sulfated or phosphatized, or a salt thereof.

2. A skin pore tightening method, comprising applying to the skin of a human having conspicuous skin pores in need thereof, a glyceryl ether derivative of the following formula (2), which is a keratinocyte contracting agent:

$$R^1O-CH_2-CH(OX^2)-CH_2-OX^1, \quad (2)$$

wherein $R^1$ is an alkyl or alkenyl group having 8 to 32 carbon atoms, and $X^1$ and $X^2$ each independently is a hydrogen atom, $-SO_2OH$ or $-PO(OH)_2$ with the proviso that $X^1$ and $X^2$ are not hydrogen atoms at the same time, or a salt thereof.

3. The skin pore tightening method according to claim 1 or 2, which comprises applying, to the skin after keratotic plugs have been removed from the skin, the keratinocyte contracting agent of the formula (1) or the salt thereof, or the glyceryl ether derivative of the formula (2) or the salt thereof.

4. The skin pore tightening method according to claim 1, comprising applying, to the skin over 8 weeks, the compound of formula (1) or the salt thereof.

5. The skin pore tightening method according to claim 2, comprising applying, to the skin over 8 weeks, the compound of formula (2) or the salt thereof.

* * * * *